(12) United States Patent
Rycroft et al.

(10) Patent No.: US 9,353,250 B2
(45) Date of Patent: May 31, 2016

(54) HINGE POLYMER

(71) Applicant: NOVA Chemicals (International) S.A., Fribourg (CH)

(72) Inventors: Jason Michael Rycroft, Strathmore (CA); Gilbert Alexander Arnould, Calgary (CA); Matthew Zaki Botros, Calgary (CA); Mark Rejman, Barrie (CA)

(73) Assignee: NOVA Chemicals (International) S.A., Fribourg (CH)

(*) Notice: Subject to any disclaimer, the term of this patent is extended or adjusted under 35 U.S.C. 154(b) by 22 days.

(21) Appl. No.: 14/205,628

(22) Filed: Mar. 12, 2014

(65) Prior Publication Data

US 2014/0275426 A1 Sep. 18, 2014

Related U.S. Application Data

(60) Provisional application No. 61/782,869, filed on Mar. 14, 2013.

(51) Int. Cl.
*C08L 23/00* (2006.01)
*C08L 23/08* (2006.01)
*G01N 3/32* (2006.01)
*G01N 3/36* (2006.01)

(52) U.S. Cl.
CPC .............. *C08L 23/0815* (2013.01); *G01N 3/32* (2013.01); *G01N 3/36* (2013.01); *G01N 2203/0023* (2013.01); *G01N 2203/0464* (2013.01)

(58) Field of Classification Search
CPC .................................................. C08L 23/0815
See application file for complete search history.

(56) References Cited

U.S. PATENT DOCUMENTS

| | | | |
|---|---|---|---|
| 4,047,495 A | | 9/1977 | O'Brian |
| 4,440,893 A | * | 4/1984 | Kallenback et al. .......... 524/305 |
| 4,638,916 A | | 1/1987 | Beck et al. |
| 5,148,912 A | | 9/1992 | Nozawa |
| 6,041,477 A | | 3/2000 | Rentsch et al. |
| 6,766,926 B1 | | 7/2004 | Elchert |
| 6,809,125 B1 | * | 10/2004 | Lee et al. ....................... 521/134 |
| 2004/0116608 A1 | * | 6/2004 | Follestad et al. .............. 525/240 |

OTHER PUBLICATIONS

ASTM D-792-13; Standard Test Methods for Density and Specific Gravity (Relative Density) of Plastics by Displacement; ASTM International; pp. 1-6.
ASTM D-1238-10; Standard Test Methods for Melt Flow Rates of Thermoplastics by Extrusion Plastometer; ASTM International; pp. 1-15.
ASTM D-790-10; Standard Test Methods for Flexural Properties of Unreinforced and Reinforced Plastics and Electrical Insulating Materials; pp. 1-11.
ASTM D-638-10; Standard Test Method for Tensile Properties of Plastics; ASTM International; pp. 1-15.
ASTM D-1525-09; Standard Test Method for Vicat Softening Temperature of Plastics; ASTM International; pp. 1-10.
ASTM D-2240-05; Standard Test Method for Rubber Property—Durometer Hardness; ASTM International; pp. 1-13.

* cited by examiner

*Primary Examiner* — Irina Krylova
(74) *Attorney, Agent, or Firm* — Lawrence T. Kale

(57) ABSTRACT

A polymer suitable for use in a thin film hinge (living hinge) comprising from about 0.1 to about 5 weight % of a $C_{4-8}$ comonomer and the balance ethylene, said composition having a density as determined according to ASTM D 792 from about 0.945 to about 0.965 $g/cm^3$; a melt index as determined according to ASTM D1238 (2.16 kg/190° C.) from about 10 to about 20 g/10 min; a weight average molecular weight (Mw) from about 45,000 to about 55,000 g/mol; a polydispersity from about 2.5 to about 3.1 and when molded into a strip having a length of about 13 cm and gross thickness from about 50 to about 70 mil (about 1 to about 2 mm) and completely bent over end to end four times to create a thinned region or crease having a thickness from about 15 to about 30 mil (about 0.3 to about 0.7 mm) tested by bending and releasing the deformed thinned region of the strip through a radius of curvature from about 180 to about 190° about a rounded plate goes through not less than 500 cycles without breaking.

5 Claims, 7 Drawing Sheets

HINGE POLYMER

FIELD OF TECHNOLOGY

Described herein are tough moldable polyethylenes. There are a number of applications where a thin molded polyethylene part is required to have excellent resistance to flex cracking. That is the part may be flexed or bent a number of times without breaking. One example is lids for dispensing containers such as condiments, spices, soaps, shampoos, oils and pills. The hinges for the lids need to have a life cycle of at least about 300 openings and closing before failure (e.g., the hinge breaks).

BACKGROUND

Currently, to the best of Applicants' knowledge, "snap top" dispensing lids are made from polypropylene due to its toughness. While polyethylene has been disclosed as being suitable it is not used in these applications. However, it is desirable from a recycling point of view to use polyethylene rather than polypropylene.

U.S. Pat. No. 4,047,495, issued Sep. 13, 1977 to O'Brian, assigned to Polytop Corporation teaches a "snap top" child proof lid for a container. The patent teaches the living hinge is preferably injection molded from polypropylene because of the well-known living hinge properties of polypropylene. Other olefin polymers can be used but are not preferred (Col. 4, lines 41-50). The patent teaches away from other polyolefins, such as polyethylene.

U.S. Pat. No. 4,638,916, issued Jan. 27, 1987 to Beck et al., assigned to Owens-Illinois, Inc., teaches a snap type hinge cap. The structural elements of the lid are disclosed but there is no disclosure of what material the lid may be made from. One of ordinary skill in the art would likely select polypropylene as the preferred material.

U.S. Pat. No. 5,148,912, issued Sep. 22, 1992 to Nozawa, assigned to Yoshino Kogyosho Co., Ltd., teaches a slightly different snap top lid in which there are two separate hinges or straps. Again the structural elements are clearly defined but the composition of the cap is not clearly specified. One of ordinary skill in the art would likely select polypropylene as the preferred material.

U.S. Pat. No. 6,041,477, issued Mar. 28, 2000 to Rentsch et al., also teaches the structural elements of a snap top lid which differ from the prior art. While the patent contains a warning about residual stress in snap top lids having adverse effects on injection moulding plastic material, (Col. 3, lines 28 to 35), nowhere in the specification is there a disclosure of suitable materials from which to make the hinge.

U.S. Pat. No. 6,766,926, issued Jul. 27, 2004 to Elchert, assigned to Owens-Illinois Closure Inc., teaches the type of closure most commonly seen today. The structural elements of the cap are clearly disclosed. However, again the material form which the cap may be made is not discussed.

A need exists to provide a polyethylene composition suitable for use in injection molding having a high resistance to cracking on repeated flexing.

SUMMARY

In its broadest embodiment, the present invention provides a polyethylene composition comprising from about 0.1 to about 5 weight % of a $C_{4-8}$ comonomer and the balance ethylene, said composition having a density as determined according to ASTM D 792 from about 0.945 to about 0.965 g/cm$^3$; a melt index as determined according to ASTM D1238 (2.16 kg/190° C.) from about 10 to about 20 g/10 min; a weight average molecular weight (Mw) from about 45,000 to about 55,000 g/mol; a polydispersity from about 2.5 to about 3.1 and when molded into a strip having a length of about 13 cm (about 5.11 inches), a gross thickness from about 50 to about 70 mil (thousandth of an inch) (about 1 to about 2 mm) and bent over end to end and released four times to create a thinned region having a thickness from about 15 to about 30 mil (thousandths of an inch) (about 0.3 to about 0.7 mm) tested by bending and releasing the deformed thinned region of the strip through a radius of curvature of about 180° to about 190°, about a plate having a rounded edge goes through not less than 200 cycles without breaking, preferably not less than 500 cycles without breaking.

In a further embodiment, the polyethylene composition has a density as determined according to ASTM D 792 from about 0.950 to about 0.960 g/cm$^3$.

In a further embodiment, the polyethylene composition has a melt index as determined according to ASTM D1238 (2.16 kg/190° C.) from about 13 to about 17 g/10 min.

In a further embodiment, the polyethylene composition when molded into a strip as above and tested as above goes through not less than 750 cycles without breaking.

In a further embodiment, the polyethylene composition has a lower comonomer content at higher molecular weight.

In a further embodiment, the polyethylene composition is prepared from one or more solution polymerized polyethylene(s).

In a further embodiment, the polyethylene composition comprises from about 60 to about 90 weight % of copolymer of ethylene and 1-butene having a density from about 0.945 to about 0.950 g/cm$^3$ as determined according to ASTM D 792; a melt index as determined according to ASTM D1238 (2.16 kg/190° C.) from about 15 to about 20 g/10 min; a weight average molecular weight (Mw) from about 45,000 to about 55,000; and a polydispersity from about 2.7 to about 3.0.

In a further embodiment, the polyethylene composition comprises of from about 40 to about 10 weight % of an ethylene homopolymer having a density from about 0.955 to about 0.965 g/cm$^3$ as determined according to ASTM D 792; a melt index as determined according to ASTM D1238 (2.16 kg/190° C.) from about 10 to about 15 g/10 min, a weight average molecular weight (Mw) from about 55,000 to about 65,000 and a polydispersity from about 3.1 to about 3.3.

In a further embodiment, the polyethylene composition consisting of from about 60 to about 80 weight % of copolymer of ethylene and 1-butene having a density from about 0.948 to about 0.952 g/cm$^3$ as determined according to ASTM D 792; a melt index as determined according to ASTM D1238 (2.16 kg/190° C.) from about 16 to about 18 g/10 min; a weight average molecular weight (Mw) from about 48,000 to about 52,000; and a polydispersity from about 2.80 to about 2.90 and from about 40 to about 20 weight % of an ethylene homopolymer having a density from about 0.960 to about 0.965 g/cm$^3$ as determined according to ASTM D 792; a melt index as determined according to ASTM D1238 (2.16 kg/190° C.) from about 12 to about 14 g/10 min, a weight average molecular weight (Mw) from about 55,000 to about 63,000 and a polydispersity from about 3.15 to about 3.25.

In a further embodiment, the polyethylene composition goes through not less than 900 cycles before breaking.

DETAILED DESCRIPTION

Figure 1:
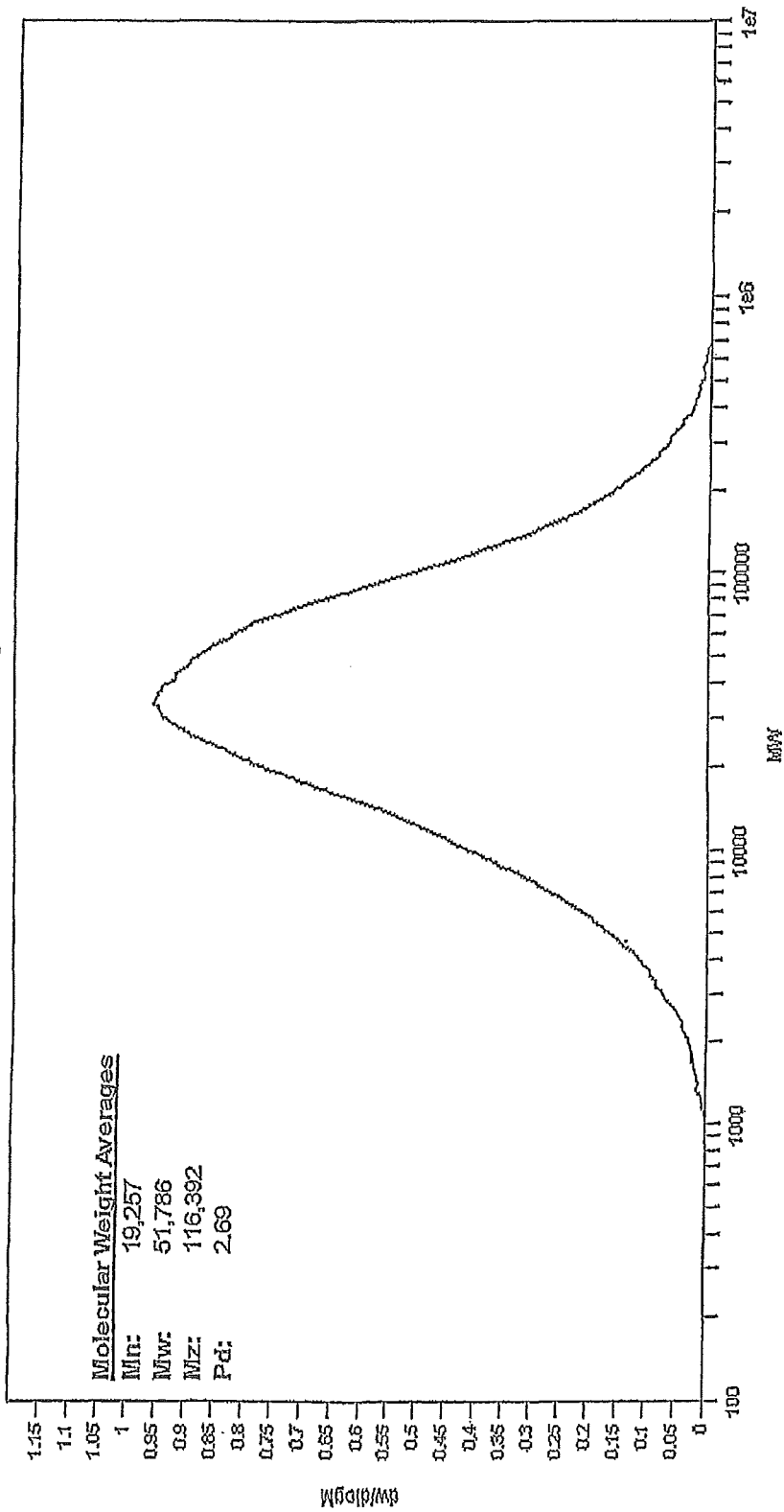
FIG. 1 is a GPC (Gel Permeation chromatography) of the blend of Example 1.

Other than in the operating examples or where otherwise indicated, all numbers or expressions referring to quantities of ingredients, reaction conditions, etc., used in the specification, and claims are to be understood as modified in all instances by the term "about." Accordingly, unless indicated to the contrary, the numerical parameters set forth in the following specification and attached claims are approximations that can vary depending upon the desired properties, which the present invention desires to obtain. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Also, it should be understood that any numerical range recited herein is intended to include all sub-ranges subsumed therein. For example, the range 1 to 5 includes 2, 3, and 4 as well as the decimal 2.1, 2.2, 2.3, . . . 4.8, 4.9 and the remaining decimal units between the end points indicated (e.g., 4.99993, 4.99994) and within the decimal ranges indicated (2.29998, 2.29999 etc.). Because the disclosed numerical ranges are continuous, they include every value between the minimum and maximum values. Unless expressly indicated otherwise, the various numerical ranges specified in this application are approximations. All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

Snap top lids are typically made using an injection molding technique. For the polymer scientist this presents several conflicting desiderata. The polymer must have sufficient stiffness (flexural modulus) so that the parts (caps) do not deform when caps are being bulk shipped to an ultimate customer. The polymer must have a melt index to permit it to quickly and completely fill the molds to make the parts (an appropriate cycle time for the part manufacturer). Finally, the polyethylene must have a sufficient bending moment. That is it can be cycled through a sufficient number of cycles through a radius of curvature of about 180 to about 190° (e.g., 90° down and then 90° up).

For example, to improve stiffness, one would seek a higher density polymer. However, this would lower the number of bending cycles to failure. One might consider increasing the molecular weight of the polymer but this would likely negatively impact on the melt index, or the ability to fill the mold quickly.

Embodiments of the polyethylene compositions described herein consist of from about 0.1 to about 5 weight %, in other cases, from about 0.2 to about 3 weight % of a $C_{4-8}$ comonomer (1-butene is a non-limiting example), and the balance ethylene, said composition having a density as determined according to ASTM D 792 from about 0.945 to about 0.965 g/cm$^3$, in other cases from about 0.950 to about 0.960 g/cm$^3$; a melt index as determined according to ASTM D1238 (2.16 kg/190° C.) from about 10 to about 20 g/10 min, in other cases from about 13 to about 17 g/10 min; a weight average molecular weight (Mw) from about 45,000 to about 55,000 g/mol, in other cases from about 48,000 to about 53,000 g/mol and in some situations from about 50,000 to about 52,000; a polydispersity (Mw/Mn) from about 2.5 to about 3.1, in other cases from 2.65 to 2.75 and in some situations from about 2.68 to about 2.71; and when molded into a strip having a length of about 13 cm and a gross thickness from about 50 to about 70 mil (about 1 to about 2 mm) and completely bent over end to end four times (preferably twice in each direction (forwards and backwards)) to create a thinned region or crease having a thickness from about 15 to about 30 mil (about 0.3 to about 0.7 mm) tested by bending and releasing the deformed thinned region of the strip through a radius of curvature from about 180 to about 190° about a plate having a rounded edge goes through not less than 200 cycles without breaking, in some cases greater than 750 cycles without breaking and in some situations greater than 900 cycles without breaking.

The polyethylene composition may have a flex modulus as determined by ASTM D 790 from about 1000 to about 1500 MPa (about 145,000 to about 220,000 psi), in some cases from about 1200 to about 1400 MPa (about 175,000 to about 200,000 psi). Polyethylene composition may have a tensile strength at yield as determined by ASTM D638 (50 mm/min) from about 20 to about 30 MPa (about 3,000 to about 4,500 psi) preferably from about 24 to about 28 MPa (about 3,600 to about 4,200 psi) and an elongation at break as determined according to ASTM D638 (50 mm/min) from about 500 to about 900%, typically from about 600 to about 800%. Generally, the softening point will be from about 120° to about 129° C., typically from about 124° to about 127° C.

The comonomer placement in the composition is usually normal to flat. The term normal refers to a comonomer placement where there is a lower amount of comonomer incorporated in the higher molecular weight fraction of the composition; the term flat refers to a comonomer placement that is approximately constant (flat) across the GPC molecular weight distribution curve of the composition.

The polyethylene compositions described herein may be a blend of two or more ethylene polymers; a non-limiting example is the blending of two ethylene polymers that are produced in a solution polymerization process. The blend may be prepared in any suitable manner; a non-limiting example is dry blending (e.g., tumble blending) the ethylene polymers and subsequent extrusion.

In one embodiment, such blends may comprise from about 60 to about 90 weight %, in some cases from about 60 to about 80, in other instances from 65 to about 75 weight % of an ethylene/1-butene copolymer containing from about 0.1 to about 5 weight %, in some cases less than about 3 weight %, in other instances less than about 1.5 weight % of 1-butene, having a density from about 0.945 to about 0.955 g/cm$^3$ as determined according to ASTM D 792, in some cases from about 0.948 to about 0.952 g/cm$^3$; a melt index as determined according to ASTM D1238 (2.16 kg/190° C.) from about 15 to about 20 g/10 min, in some cases from about 16 to about 18 g/10 min; a weight average molecular weight (Mw) from about 45,000 to about 55,000, in some cases from about 48,000 to about 52,000, in other instances from about 49,000 to 51,000 g/mol; and a polydispersity from about 2.7 to about 3.0, in some cases from about 2.8 to about 2.9, in other instances from about 2.84 to about 2.88.

The copolymer may have a flex modulus as determined by ASTM D 790 from about 900 to about 1200 MPa (about 130,000 to about 175,000 psi), in some cases from about 1000 to about 1100 MPa (about 145,000 to about 160,000 psi).

The copolymer may have a tensile strength at yield as determined by ASTM D638 (50 mm/min) from about 22 to about 24 MPa (about 3,300 to about 3,600 psi) and an elongation at break as determined according to ASTM D638 (50 mm/min) from about 500 to about 550%, in some cases from about 520 to about 540%. Generally, the softening point will be about 118° C. to about 122° C., in some cases from about 119° C. to about 121° C.

In a further embodiment, the polyethylene composition comprises of from about 40 to about 10 weight %, in some cases, from about 40 to about 20 weight %, in other instances, from about 35 to 25 weight % of an ethylene homopolymer having a density from about 0.958 to about 0.965 g/cm$^3$ as determined according to ASTM D 792, in other cases, from about 0.960 to about 0.963 g/cm$^3$; a melt index as determined according to ASTM D1238 (2.16 kg/190° C.) from about 10 to about 15 g/10 min, in other cases, from about 12 to about 14 g/10 min, a weight average molecular weight (Mw) from about 55,000 to about 65,000, in some cases, from about 56,000 to about 63,000, in other instances, from about 56,000 to about 58,000 g/mol and a polydispersity from about 3.1 to about 3.3, in some cases from about 3.15 to about 3.25, in other instances, from about 3.15 to about 3.20.

The homopolymer may have a flex modulus as determined by ASTM D 790 from about 1100 to about 1300 MPa (about 160,000 to about 190,000 psi), in some cases from about 1200 to about 1300 MPa (about 175,000 to about 190,000 psi).

The homopolymer may have a tensile strength at yield as determined by ASTM D638 (50 mm/min) from about 28 to about 34 MPa (about 4,050 to about 4,900 psi), in some cases, from about 28 to about 32 MPa (about 4,050 to about 4,600 psi) and an elongation at break as determined according to ASTM D638 (50 mm/min) from about 700 to about 900%, in some cases, from about 750 to about 850%. Generally, the softening point will be about 128° C. to about 131° C., in some cases, from about 129° C. to about 130° C.

In another embodiment, the polyethylene composition comprises a blend of the above ethylene/1-butene copolymer and the ethylene homopolymer. This embodiment, or blend, may comprise from about 60 to about 90 weight %, in some cases, from about 60 to about 80 weight %, in other instances, from about 65 to about 75 weight % of the ethylene/1-butene copolymer and from about 40 to about 10 weight %, in some cases, from about 40 to about 20 weight %, in other instances, from about 35 to about 25 weight % of the ethylene homopolymer.

The polyethylene polymers suitable for use in the present invention may be prepared using conventional polymerization processes; non-limiting examples include gas phase, slurry and solution polymerization. The polyethylenes may be prepared using conventional catalysts. Non-limiting examples of conventional catalysts include; chrome based catalysts, Ziegler-Natta catalysts and single site catalysts. Such processes and catalyst are well known to those skilled in the art.

Solution and slurry polymerization processes are fairly well known in the art. These processes are conducted in the presence of an inert hydrocarbon solvent/diluent in some cases a $C_{4-12}$ hydrocarbon which may be unsubstituted or substituted by a $C_{1-4}$ alkyl group, such as, butane, pentane, hexane, heptane, octane, cyclohexane, methylcyclohexane or hydrogenated naphtha. A non-limiting example of a commercial solvent is Isopar E ($C_{8-12}$ aliphatic solvent, Exxon Chemical Co.). The monomers are dissolved in the solvent/diluent.

The polymerization may be conducted at temperatures from about 20° C. to about 250° C. Depending on the product being made, this temperature may be relatively low such as from about 20° C. to about 180° C., in other cases, from about 80° C. to about 150° C. and the polymer is insoluble in the liquid hydrocarbon phase (diluent) (e.g., a slurry polymerization). The reaction temperature may be relatively higher from about 180° C. to about 250° C., in other cases, from about 180° C. to about 230° C. and the polymer is soluble in the liquid hydrocarbon phase (solvent) (e.g., a solution polymerization). The pressure of the reaction may be as high as about 15,000 psig for the older high pressure processes or may range from about 15 to about 4,500 psig.

The polymerization could be gas phase, either fluidized bed or stirred bed. In the gas phase polymerization of a gaseous mixture comprising from about 0 to about 15 mole % of hydrogen, from about 0 to about 30 mole % of one or more $C_{3-8}$ alpha-olefins, from about 15 to about 100 mole % of ethylene, and from about 0 to about 75 mole % of an inert gas at a temperature from about 50° C. to about 120° C., in some cases from about 75° C. to about 110° C., and at pressures not exceeding about 3447 kPa (about 500 psi), in other cases not greater than about 2414 kPa (about 350 psi).

Suitable olefin monomers include ethylene and $C_{3-8}$ alpha olefins such as one or more of 1-butene, 1-hexene, and 1-octene. The polymers prepared in accordance with the present invention may have a wide range of molecular weight distribution (Mw/Mn or polydispersity). The molecular weight distribution may be controlled from about 2.5 to about 30.

In one embodiment, the polymers are solution polymers prepared in the presence of a Ziegler-Natta catalyst; wherein the final composition comprises at least one copolymer of ethylene and 1-butene.

The resulting resin may typically be compounded either by the manufacturer or the converter (e.g., the company converting the resin pellets into the final product). The compounded polymer may contain fillers, pigments and other additives. Typically, the fillers are inert additives, such as, clay, talc, $TiO_2$ and calcium carbonate, which may be added to the polyolefin in amounts from about 0 weight % up to about 50 weight %, in some cases, less than 30 weight % of fillers are added. The resin may contain typical amounts of antioxidants and heat and light stabilizers, such as, combinations of one or more of hindered phenols, phosphates, phosphites and phosphonites, typically, in amounts of less than about 0.5 weight % based on the weight of the resin. Pigments may also be added to the resin in small amounts; non-limiting examples of pigments include carbon black, phthalocyanine blue, Congo red, titanium yellow, etc.

The polyethylene resin blend may contain a nucleating agent in amounts from about 1,500 parts per million (ppm) to about 10,000 ppm based on the weight of the polyolefin. In some cases, the nucleating agent is used in amounts from about 2,000 ppm to about 8,000 ppm, in other instances, from about 2,000 ppm to about 5,000 ppm based on the weight of the polyolefin.

The nucleating agent may be selected from the group consisting of dibenzylidene sorbitol, di(p-methyl benzylidene) sorbitol, di(o-methyl benzylidene) sorbitol, di(p-ethylbenzylidene) sorbitol, bis(3,4-dimethyl benzylidene) sorbitol, bis(3,4-diethylbenzylidene) sorbitol and bis(trimethyl-benzylidene) sorbitol. One commercially available nucleating agent is bis(3,4-dimethyl benzylidene) sorbitol.

Since the resin is used in caps typically for food contact applications, the additive package must meet the appropriate food regulations, such as, the FDA regulations in the United States.

Figure 6:
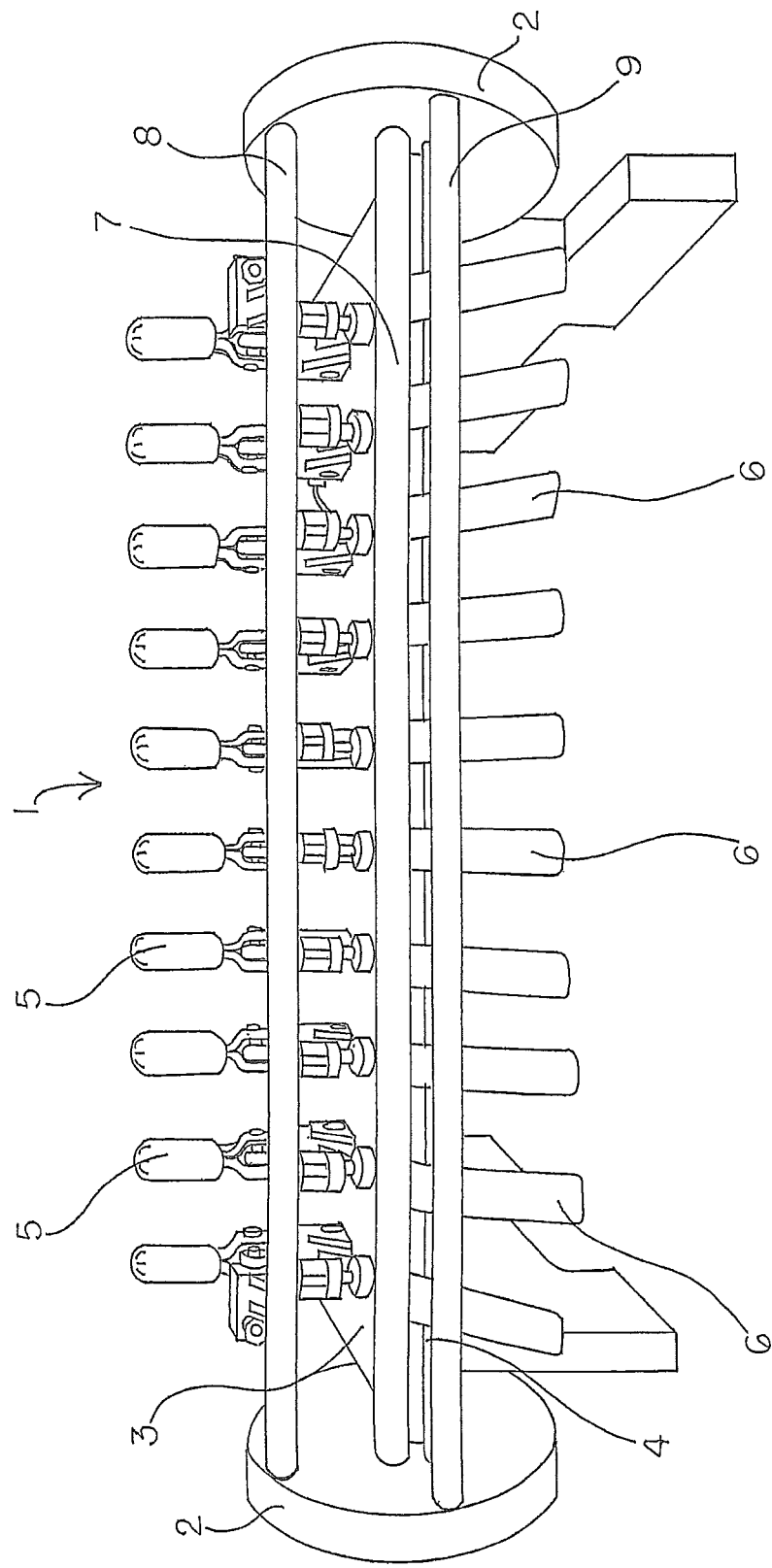
FIG. 6 is a front photograph of the bending strip tester used in the experiments.

The polymer is tested for the number of bend and release cycles by compression molding a strip having thickness from about 50 to about 70 mil (about 1 to about 2 mm) and a length of about 13 cm and completely bent over end to end and opened four times or cycles to create a thinned region or crease having a thickness from about 15 to about 30 mil (about 0.3 to about 0.7 mm). The strip is mounted in a device as shown in FIG. 6 with the thinned area or crease over or adjacent the edged of a rounded plate (to avoid cutting the strip curing testing). The device bends the strip over the edge of the plate through a radius of curvature of about 180° to about 190° (i.e., one cycle is 90° up and then 90° down). The number of cycles until the test strip breaks is recorded. Generally, ten strips of the same polymer are tested at the same time and the result is an average value until break.

The following example is intended to aid in understanding the present invention, however, in no way, should this example be interpreted as limiting the scope thereof.

Example 1

Figure 2:
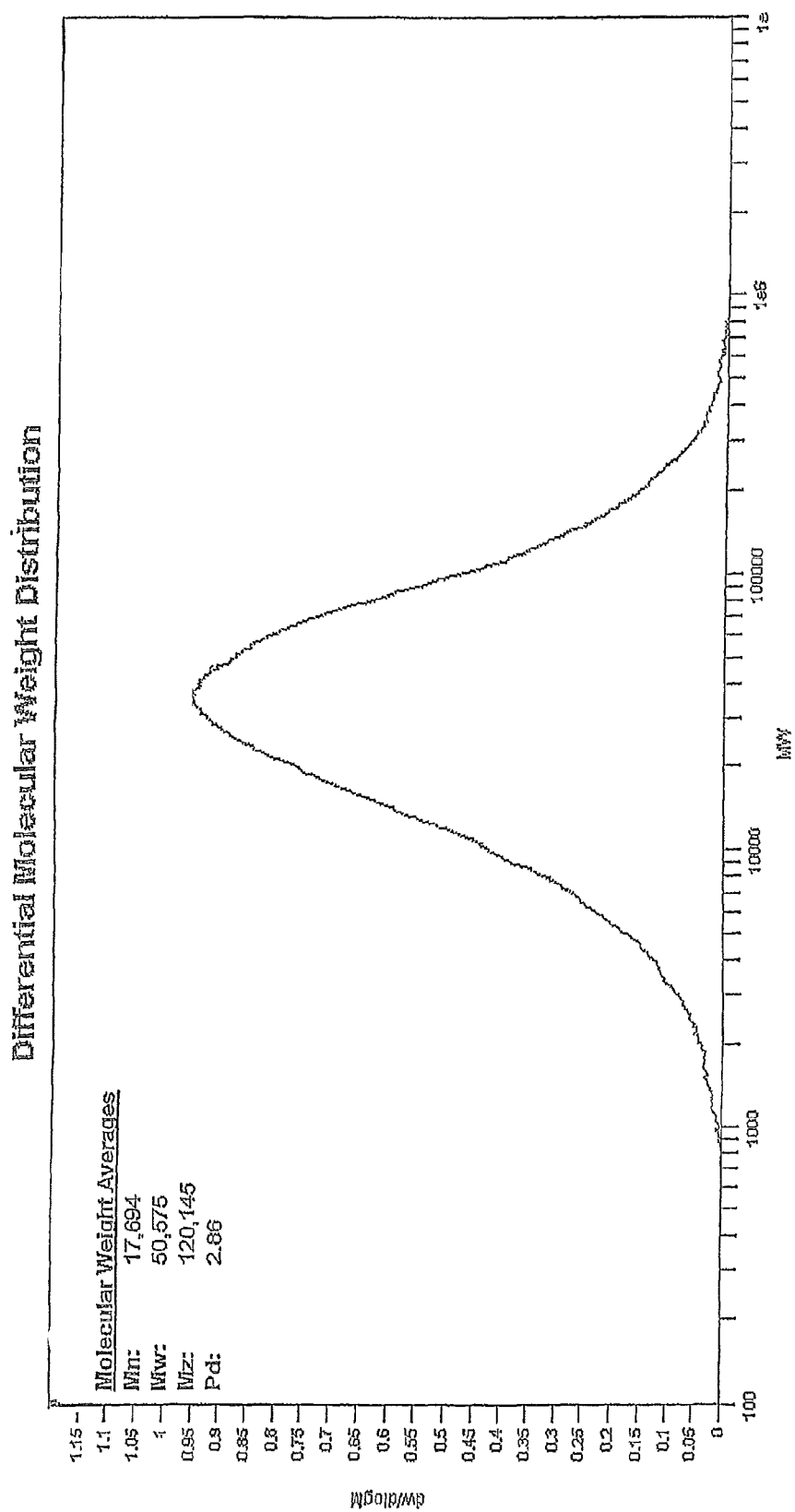
FIG. 2 is a GPC of the copolymer used in Example 1.
Figure 3:
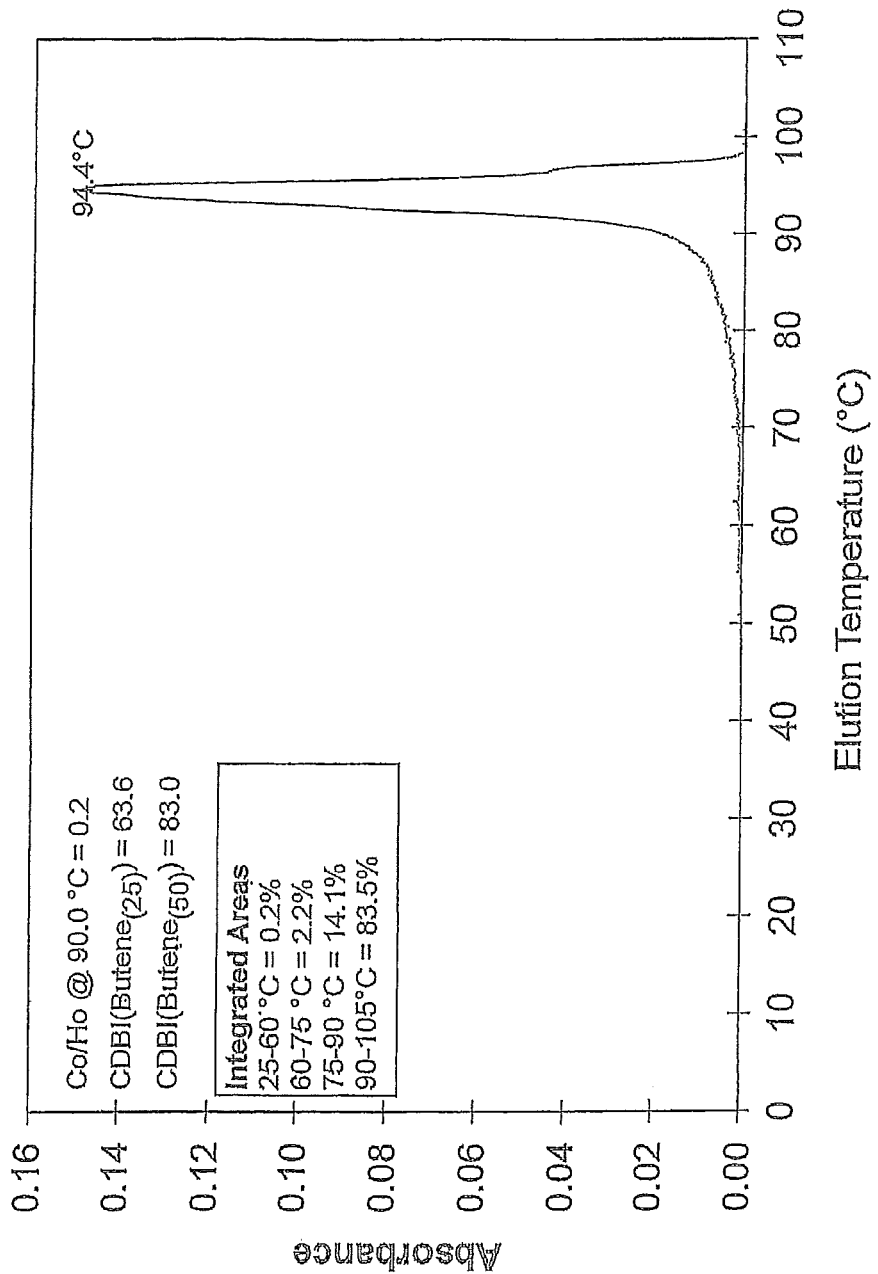
FIG. 3 is an A-TREF of the copolymer used in Example 1.
Figure 4:
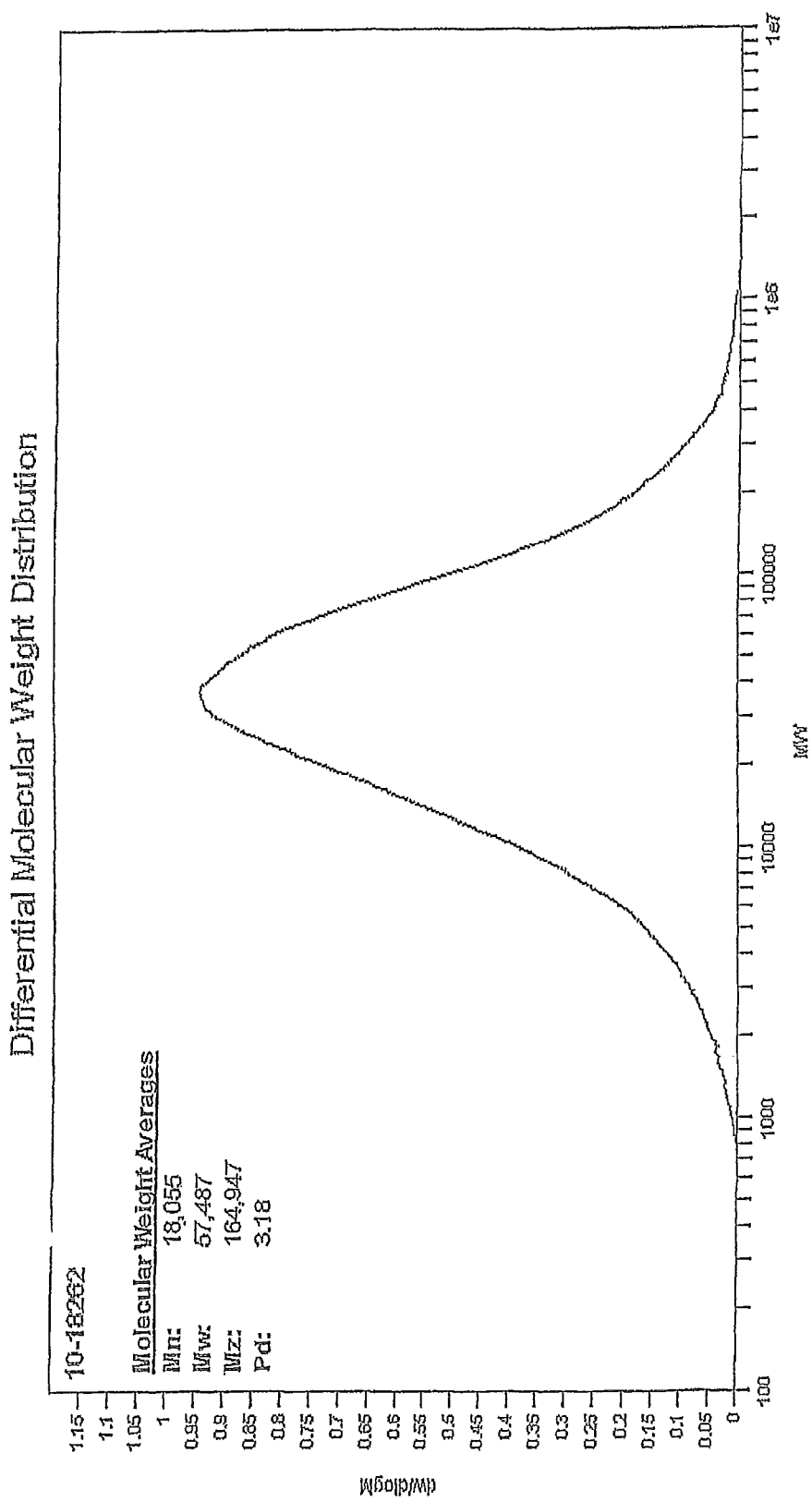
FIG. 4 is a GPC of the homopolymer used in Example 1.
Figure 5:
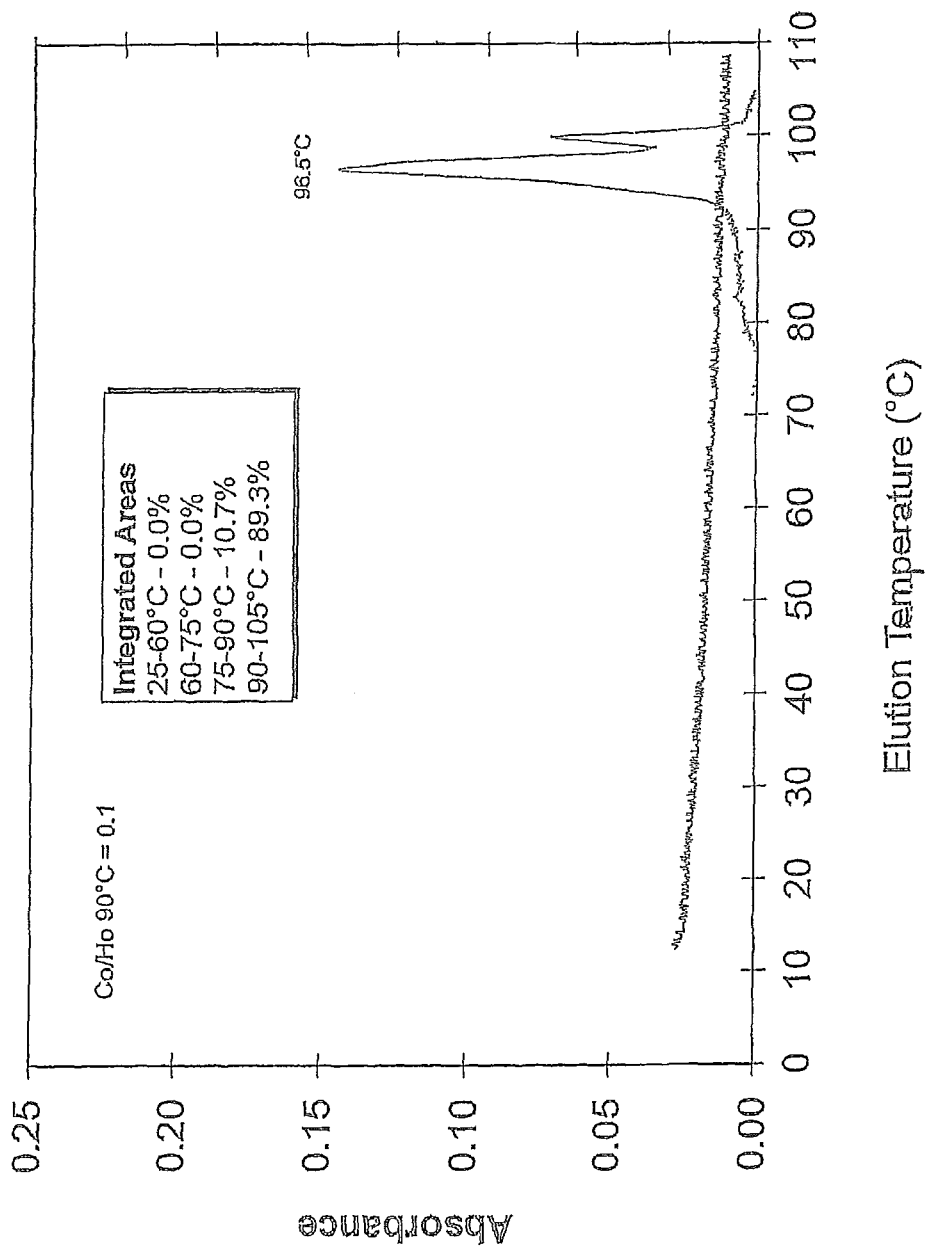
FIG. 5 is an A-TREF of the homopolymer used in Example 1.

The following resins were used in Example 1: SCLAIR polyethylene resins 2710 and 2909. SCLAIR 2710 is a copolymer of ethylene and about 0.35 wt. % of 1-butene. SCLAIR 2909 is a homopolymer of ethylene. The GPC curve and the A-TREF curves for copolymer SCLAIR 2710 are shown in FIGS. 2 and 3, respectively. The GPC curve and the A-TREF curves for homopolymer SCLAIR 2909 are shown in FIGS. 4 and 5, respectively.

Table 1 summarizes the polymer properties.

TABLE 1

| Property | Test Method ASTM | Units | SCLAIR 2710 typical values | SCLAIR 2909 typical values |
|---|---|---|---|---|
| Melt Index | D 1238 | g/10 min | 17 | 13 |
| Density | D 792 | g/cm$^3$ | 0.951 | 0.962 |
| Tensile Strength at Yield 50 mm/min | D 638 | MPa (psi) | 23 (3400) | 29 (4200) |
| Elongation at break | D 638 | % | 530 | 800 |
| Flexural Modulus | D 790 | MPa (psi) | 1000 (145000) | 1280 (185000) |
| Hardness Shore D | D 2240 |  | 62 | 65 |
| Softening point | D 1525 | ° C. (° F.) | 120 (248) | 129 (264) |

The resins were tested in a blend, denoted Example 1, comprising 70 wt % of the copolymer and 30 weight % of the homopolymer. The GPC curve of Example 1 is shown in FIG. 1.

Example 1 was molded into polymer strip samples as described above.

Figure 7:
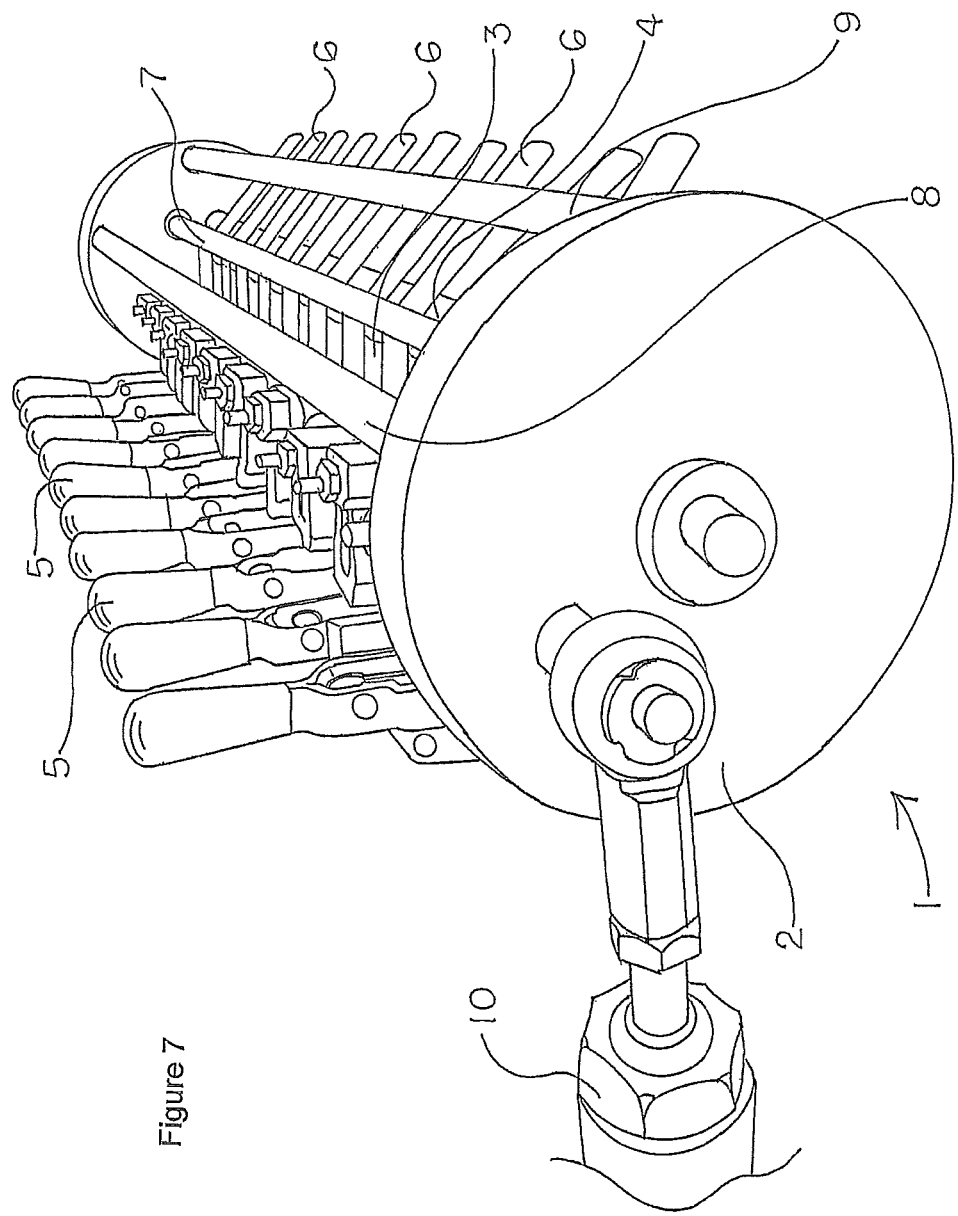
FIG. 7 is a side photograph of the bending strip tester used in the experiments.

Polymer strip testing was done in a machine shown in FIGS. 6 and 7 in which like parts have like numbers. The machine generally shown at 1 comprises a pair of pivoting disks 2 having there between a flat plate 3 having a rounded edge or lip 4. On top of the plate are a series of clamps 5 adjacent to edge or lip 4, which are attached to the plate 3. The test strips 6 are mounded on the plate 3 with clamps 5 and positioned so that one end of the strip is held by a clamp. The crease or thinned area is placed over the edge or lip 4. There is a bar 7 mounted between the disks 2 which rests on top of the test strips 6 inside of the rounded edge or lip 4. A further pair of bars 8 and 9 are mounted spaced apart between the disks 2. Disks 2 are driven by hydraulic pistons 10 and 11 (not shown) to cycle spaced apart bars 8 and 9 through a radius of curvature from 90° above the plate 3 to 90° below plate 3. The bars engage the end of the test strips 6 to bend them through each cycle. The number of cycles at which a test strip breaks is recorded. Typically, 10 strips are tested at the same time and the average number of cycles to break is recorded. FIG. 7 shows hydraulic piston 10 attached to pivoting disk 2 (hydraulic piston 11 is not shown).

The results of the testing are set forth in Table 2 below.

TABLE 2

| Strip Hinge Raw Data Cycles to Failure | | | | | | | | | | |
|---|---|---|---|---|---|---|---|---|---|---|
| Date of Analysis | March 12/2013 | | | | | | | | | |
| Resin Grade: | Blended 70% SCLAIR® 2710/30% SCLAIR® 2909 | | | | | | | | | |
| Temperature: | Ambient Lab | | | | | | | | | |
| Color: | White | | | | | | | | | |
| Test Station | 1 | 2 | 3 | 4 | 5 | 6 | 7 | 8 | 9 | 10 |
| min. | 1032 | 1015 | 978 | 1824 | 1769 | 2493 | 650 | 1769 | 859 | 2086 |
| max. | 1165 | 1032 | 1015 | 1922 | 1824 | 2510 | 859 | 1824 | 873 | 2260 |

Overall Cycles to Failure:
Ave. = 1487.95
Range: min. = 650 max. = 2510
notes:
This sample was compression molded.

While the present invention has been particularly set forth in terms of specific embodiments thereof, it will be understood in view of the instant disclosure that numerous variations upon the invention are now enabled yet reside within the scope of the invention. Accordingly, the invention is to be broadly construed and limited only by the scope and spirit of the claims now appended hereto.

What is claimed is:

1. A polyethylene composition consisting of:
   i) from 60 to 80 weight % of a polyethylene consisting of: from 0.1 to 0.5 weight of 1-butene and the balance ethylene, said composition having a density as determined according to ASTM D 792 from 0.948 to 0.952 g/cm$^3$; a melt index as determined according to ASTM D1238 (2.16 kg 190° C.) from 16 to 18 g/10 min; a weight average molecular weight (Mw) from 48,000 to 52,000 g/mol; a polydispersity from 2.7 to 3.0 and;
   ii) from 40 to 20 wt. % of a polyethylene homopolymer having a density from 0.960 g/cm$^3$ to 0.965 g/cm$^3$; a melt index as determined according to ASTM D1238 (2.16 kg 190° C.) from 12 to 14 g/10 min, a weight average molecular weight (Mw) from 55,000 to 63,000 and a polydispersity from 3.0 to 3.3;
   wherein said polyethylene composition has a density according to ASTM 792 from 0.950 to 0.960 g/cm$^3$, a tensile strength at yield from 24 to 28 MPa, and when molded into a strip having a length of 13 cm and gross thickness from 50 to 70 mil (1 to 2 mm) and completely bent over end to end four times to create a creased strip having a thinned region having a thickness from 15 to 30 mil (0.3 to 0.3 mm); said creased strip is tested in a bending and releasing cycle until breaking; wherein said thinned region is bent and released through a radius of curvature of 180° to 190° about a rounded plate until said creased strap breaks; wherein said creased strip goes through from about 650 to 2510 cycles prior to breaking.

2. The polyethylene composition according to claim 1, wherein said creased strip goes through from about 750 to 2510 bending and releasing cycles prior to breaking.

3. The polyethylene composition according to claim 1, wherein the polyethylene composition has a lower comonomer content at higher molecular weight.

4. The polyethylene composition according to claim 1, wherein component i) and component ii) are solution polymerized.

5. The polyethylene composition according to claim 1, wherein said creased strip through from about 900 to 2510 bending and releasing cycles prior to breaking.

* * * * *